United States Patent
Bartholomew

(10) Patent No.: US 10,458,904 B2
(45) Date of Patent: Oct. 29, 2019

(54) DIFFERENTIAL ABSORPTION LIDAR

(71) Applicant: Ball Aerospace & Technologies Corp., Boulder, CO (US)

(72) Inventor: Jarett Levi Bartholomew, Longmont, CO (US)

(73) Assignee: Ball Aerospace & Technologies Corp., Boulder, CO (US)

( * ) Notice: Subject to any disclaimer, the term of this patent is extended or adjusted under 35 U.S.C. 154(b) by 378 days.

(21) Appl. No.: 15/279,177

(22) Filed: Sep. 28, 2016

(65) Prior Publication Data

US 2017/0089829 A1 Mar. 30, 2017

Related U.S. Application Data

(60) Provisional application No. 62/233,768, filed on Sep. 28, 2015.

(51) Int. Cl.
*G01N 21/31* (2006.01)
*G01J 3/02* (2006.01)
(Continued)

(52) U.S. Cl.
CPC ........ *G01N 21/3151* (2013.01); *G01J 3/0254* (2013.01); *G01N 21/255* (2013.01);
(Continued)

(58) Field of Classification Search
CPC ...... G01S 17/32; G01S 7/499; G01N 21/3151
See application file for complete search history.

(56) References Cited

U.S. PATENT DOCUMENTS 3,856,402 A 12/1974 Low et al.
3,925,666 A 12/1975 Allan et al.
(Continued)

FOREIGN PATENT DOCUMENTS

CA 1305767 7/1992
CA 2509540 7/2004
(Continued)

OTHER PUBLICATIONS

Mitchell et al. "Remote Methane Sensor Using Tuneable Diode Laser Spectroscopy (TDLS) Via a 1W Raman Source," Proceedings of SPIE, Oct. 2009, vol. 7503, 750350, 4 pages.
(Continued)

*Primary Examiner* — Eric L Bolda
(74) *Attorney, Agent, or Firm* — Sheridan Ross P.C.

(57) ABSTRACT

A system for remotely detecting gas concentration is provided. The system includes a plurality of light sources. At least a first one of the light sources generates light having a first wavelength and a first polarization, and at least a second one of the light sources generates light having a second, different wavelength and a second polarization that is orthogonal to the first polarization. The light from the light sources is placed on a common transmission path, and is directed to a target area by a steering mirror. Light reflected from the target area is received and directed to a detector. The detector provides information regarding the time of arrival and amplitude of the received light, allowing range and gas concentration information to be obtained. In some embodiments the detector is an imaging detector, allowing three-dimensional range information to be obtained from the target area from a single light pulse.

21 Claims, 6 Drawing Sheets

(51) Int. Cl.

| | | |
|---|---|---|
| *G01N 21/25* | (2006.01) | |
| *G01S 7/481* | (2006.01) | |
| *G01S 17/02* | (2006.01) | |
| *G01S 17/89* | (2006.01) | |
| *G01J 3/10* | (2006.01) | |
| *G01J 3/28* | (2006.01) | |
| *G01J 3/42* | (2006.01) | |
| *G01S 7/497* | (2006.01) | |
| *G01S 7/499* | (2006.01) | |

(52) U.S. Cl.
CPC .......... *G01S 7/4818* (2013.01); *G01S 17/023* (2013.01); *G01S 17/89* (2013.01); *G01N 2201/068* (2013.01); *G01N 2201/06113* (2013.01)

(56) References Cited

U.S. PATENT DOCUMENTS

| | | |
|---|---|---|
| 4,022,532 A | 5/1977 | Montagnino |
| 4,059,356 A | 11/1977 | Kebabian |
| 4,201,468 A | 5/1980 | Margolis et al. |
| 4,286,877 A | 9/1981 | Clarke |
| 4,425,503 A | 1/1984 | Watkins et al. |
| 4,450,356 A | 5/1984 | Murray et al. |
| 4,489,239 A | 12/1984 | Grant et al. |
| 4,567,366 A | 1/1986 | Shinohara |
| 4,730,320 A | 3/1988 | Hidaka et al. |
| 4,772,789 A | 9/1988 | Maram et al. |
| 4,870,275 A | 9/1989 | Ozdemir |
| 5,001,346 A | 3/1991 | Barkhoudarian |
| 5,015,099 A | 5/1991 | Nagai et al. |
| 5,029,023 A | 7/1991 | Bearden et al. |
| 5,087,125 A | 2/1992 | Narutaki |
| 5,091,778 A | 2/1992 | Keeler |
| 5,149,959 A | 9/1992 | Collins et al. |
| 5,157,257 A | 10/1992 | Geiger |
| 5,179,422 A * | 1/1993 | Peterson ................ G01N 21/94 250/559.41 |
| 5,192,978 A | 3/1993 | Keeler |
| 5,239,860 A | 8/1993 | Harris et al. |
| 5,250,810 A | 10/1993 | Geiger |
| 5,262,645 A | 11/1993 | Lambert et al. |
| 5,298,751 A | 3/1994 | Fee et al. |
| 5,317,376 A | 5/1994 | Amzajerdi et al. |
| 5,345,304 A | 9/1994 | Allen |
| 5,357,371 A | 10/1994 | Minott |
| 5,485,009 A | 1/1996 | Meyzonnetie et al. |
| 5,528,354 A | 6/1996 | Uwira |
| 5,544,186 A | 8/1996 | Sauer et al. |
| 5,552,893 A | 9/1996 | Akasu |
| 5,682,225 A | 10/1997 | DuBois et al. |
| 5,682,229 A | 10/1997 | Wangler |
| 5,767,519 A | 6/1998 | Gelbwachs |
| 5,784,023 A | 6/1998 | Bluege |
| 5,790,188 A | 8/1998 | Sun |
| 5,793,034 A | 8/1998 | Wesolowicz et al. |
| 5,815,250 A | 9/1998 | Thomson et al. |
| 5,847,816 A | 12/1998 | Zediker et al. |
| 5,870,180 A | 2/1999 | Wangler |
| 5,870,181 A | 2/1999 | Andressen |
| 5,914,776 A | 6/1999 | Streicher |
| 5,917,596 A | 6/1999 | Jenkins et al. |
| 5,923,466 A | 7/1999 | Krause et al. |
| 6,034,770 A | 3/2000 | Kim et al. |
| 6,173,066 B1 | 1/2001 | Peurach et al. |
| 6,323,941 B1 | 11/2001 | Evans et al. |
| 6,327,037 B1 * | 12/2001 | Chou ................ G01J 4/04 356/484 |
| 6,384,903 B1 | 5/2002 | Fuller |
| 6,411,871 B1 | 6/2002 | Lin |
| 6,414,746 B1 | 7/2002 | Stettner et al. |
| 6,434,211 B1 | 8/2002 | Lloyd et al. |
| 6,448,572 B1 | 9/2002 | Tennant et al. |
| 6,509,566 B1 | 1/2003 | Wamsley et al. |
| 6,542,831 B1 | 4/2003 | Moosmuller et al. |
| 6,597,505 B1 * | 7/2003 | Chaney .............. G01B 9/02007 356/338 |
| 6,608,669 B2 | 8/2003 | Holton et al. |
| 6,646,725 B1 | 11/2003 | Eichinger et al. |
| 6,657,733 B1 | 12/2003 | Drake |
| 6,664,529 B2 | 12/2003 | Pack et al. |
| 6,665,063 B2 | 12/2003 | Jamieson et al. |
| 6,690,472 B2 | 2/2004 | Kulp et al. |
| 6,697,155 B2 | 2/2004 | Dobbs et al. |
| 6,747,258 B2 | 6/2004 | Benz et al. |
| 6,804,607 B1 | 10/2004 | Wood |
| 6,822,742 B1 | 11/2004 | Kalayeh et al. |
| 6,943,868 B2 | 9/2005 | Haig |
| 6,972,887 B2 | 12/2005 | Wickham et al. |
| 7,006,203 B1 | 2/2006 | Book et al. |
| 7,027,924 B2 | 4/2006 | Spoonhower et al. |
| 7,067,812 B2 | 6/2006 | Gelbwachs |
| 7,075,653 B1 | 7/2006 | Rutherford |
| 7,095,488 B2 | 8/2006 | Jamieson et al. |
| 7,113,886 B2 | 9/2006 | West |
| 7,142,981 B2 | 11/2006 | Hablani |
| 7,221,436 B1 | 5/2007 | Mendenhall et al. |
| 7,224,466 B2 | 5/2007 | Ray |
| 7,224,707 B2 | 5/2007 | Gendron |
| 7,236,235 B2 | 6/2007 | Dimsdale |
| 7,240,879 B1 | 7/2007 | Cepollina et al. |
| 7,260,507 B2 | 8/2007 | Kalayeh |
| 7,277,641 B1 | 10/2007 | Gleckman |
| 7,298,869 B1 | 11/2007 | Abernathy |
| 7,312,452 B2 | 12/2007 | Klingenberg et al. |
| 7,333,184 B2 | 2/2008 | Kalayeh |
| 7,342,228 B1 | 3/2008 | O'Connell et al. |
| 7,345,743 B1 | 3/2008 | Hartman et al. |
| 7,349,094 B2 | 3/2008 | Harris et al. |
| 7,359,057 B2 | 4/2008 | Schwiesow |
| 7,361,922 B2 | 4/2008 | Kameyama et al. |
| 7,385,705 B1 | 6/2008 | Hoctor et al. |
| 7,397,568 B2 | 7/2008 | Bryce et al. |
| 7,406,220 B1 | 7/2008 | Christensen et al. |
| 7,411,196 B2 | 8/2008 | Kalayeh |
| 7,414,726 B1 | 8/2008 | Bambeck |
| 7,414,727 B2 | 8/2008 | Willing et al. |
| 7,436,494 B1 | 10/2008 | Kennedy et al. |
| 7,453,552 B1 | 11/2008 | Miesak et al. |
| 7,456,970 B1 | 11/2008 | Lopez et al. |
| 7,474,685 B2 | 1/2009 | Kalayeh |
| 7,486,399 B1 | 2/2009 | Reichardt et al. |
| 7,508,520 B1 | 3/2009 | Lines et al. |
| 7,532,311 B2 | 5/2009 | Henderson et al. |
| 7,580,132 B2 | 8/2009 | Baillon et al. |
| 7,705,988 B2 | 4/2010 | Richman |
| 7,755,041 B2 | 7/2010 | Killinger et al. |
| 7,961,301 B2 | 6/2011 | Earhart et al. |
| 7,995,917 B2 | 8/2011 | Mendenhall et al. |
| 8,010,300 B1 | 8/2011 | Stearns et al. |
| 8,013,303 B2 | 9/2011 | Ershov et al. |
| 8,077,294 B1 | 12/2011 | Grund et al. |
| 8,121,798 B2 | 2/2012 | Lippert et al. |
| 8,229,679 B1 | 7/2012 | Matthews |
| 8,269,971 B1 | 9/2012 | Marsh et al. |
| 8,294,899 B2 | 10/2012 | Wong |
| 8,306,273 B1 | 11/2012 | Grayseth et al. |
| 8,345,250 B1 | 1/2013 | Janosky et al. |
| 8,379,208 B1 | 2/2013 | Simmons et al. |
| 8,395,771 B2 | 3/2013 | Izawa et al. |
| 8,559,721 B1 | 10/2013 | Bartholomew et al. |
| 8,730,461 B2 | 5/2014 | Andresi |
| 8,736,818 B2 | 5/2014 | Weimer et al. |
| 8,781,755 B2 | 7/2014 | Wong |
| 8,823,938 B2 | 9/2014 | Beck et al. |
| 9,030,663 B2 | 5/2015 | Braun et al. |
| 9,037,413 B1 | 5/2015 | Rodgers et al. |
| 9,097,646 B1 | 8/2015 | Campbell et al. |
| 9,442,012 B2 | 9/2016 | Mann et al. |
| 9,534,893 B2 | 1/2017 | Tulet et al. |
| 2002/0117340 A1 | 8/2002 | Stettner |
| 2002/0118352 A1 | 8/2002 | Ohzu et al. |

(56) References Cited

U.S. PATENT DOCUMENTS

| | | |
|---|---|---|
| 2003/0030001 A1 | 2/2003 | Cooper et al. |
| 2003/0063884 A1 | 4/2003 | Smith et al. |
| 2004/0021852 A1 | 2/2004 | DeFlumere |
| 2004/0119838 A1 | 6/2004 | Griffis et al. |
| 2004/0130702 A1 | 7/2004 | Jupp et al. |
| 2004/0213463 A1 | 10/2004 | Morrison |
| 2004/0263852 A1 | 12/2004 | Degtiarev et al. |
| 2005/0018743 A1 | 1/2005 | Volodin et al. |
| 2005/0052636 A1 | 3/2005 | Lee et al. |
| 2005/0060092 A1 | 3/2005 | Hablani |
| 2005/0099634 A1 | 5/2005 | Dubois et al. |
| 2005/0160822 A1 | 7/2005 | Langdon |
| 2006/0088946 A1 | 4/2006 | Willson et al. |
| 2006/0114447 A1 | 6/2006 | Harris et al. |
| 2006/0132752 A1 | 6/2006 | Kane |
| 2006/0136172 A1 | 6/2006 | O'Kane et al. |
| 2006/0197936 A1 | 9/2006 | Liebman et al. |
| 2006/0203248 A1 | 9/2006 | Reichardt et al. |
| 2007/0018104 A1 | 1/2007 | Parvin et al. |
| 2007/0073486 A1 | 3/2007 | Tillotson et al. |
| 2007/0090861 A1* | 4/2007 | Andersen ............... G02F 3/026 327/123 |
| 2007/0110364 A1 | 5/2007 | Rice et al. |
| 2007/0115541 A1 | 5/2007 | Rogers et al. |
| 2007/0122001 A1 | 5/2007 | Wang et al. |
| 2007/0171407 A1 | 7/2007 | Cole et al. |
| 2007/0263676 A1 | 11/2007 | Beukema et al. |
| 2008/0023587 A1 | 1/2008 | Head et al. |
| 2008/0136626 A1 | 6/2008 | Hudson et al. |
| 2008/0212328 A1 | 9/2008 | Minano et al. |
| 2008/0259340 A1 | 10/2008 | Prasad et al. |
| 2008/0273560 A1 | 11/2008 | Stelmakh |
| 2008/0290259 A1 | 11/2008 | Mathewson et al. |
| 2008/0316498 A1 | 12/2008 | Drake et al. |
| 2009/0002680 A1 | 1/2009 | Ruff et al. |
| 2009/0046289 A1 | 2/2009 | Caldwell et al. |
| 2009/0059201 A1 | 3/2009 | Willner et al. |
| 2009/0080695 A1 | 3/2009 | Yang |
| 2009/0110267 A1 | 4/2009 | Zakhor et al. |
| 2009/0115994 A1 | 5/2009 | Stettner et al. |
| 2009/0142066 A1 | 6/2009 | Leclair et al. |
| 2009/0237640 A1 | 9/2009 | Krikorian et al. |
| 2009/0273770 A1 | 11/2009 | Bauhahn et al. |
| 2009/0310118 A1 | 12/2009 | Halldorsson |
| 2010/0110204 A1 | 5/2010 | Campbell et al. |
| 2010/0165323 A1 | 6/2010 | Fiess et al. |
| 2010/0182587 A1 | 7/2010 | Fluckiger |
| 2010/0315631 A1 | 12/2010 | Zhou et al. |
| 2011/0038507 A1 | 2/2011 | Hager |
| 2011/0074931 A1 | 3/2011 | Bilbrey et al. |
| 2011/0222063 A1 | 9/2011 | Izawa et al. |
| 2012/0154813 A1 | 6/2012 | Li et al. |
| 2012/0163791 A1 | 6/2012 | Juri et al. |
| 2013/0242131 A1 | 9/2013 | Timm |
| 2013/0335599 A1 | 12/2013 | Zhang |
| 2014/0158870 A1 | 6/2014 | DeAntonio et al. |
| 2014/0300798 A1 | 10/2014 | Sapir |
| 2014/0362880 A1 | 12/2014 | Chuang et al. |
| 2015/0022809 A1 | 1/2015 | Marchant et al. |
| 2015/0323449 A1 | 11/2015 | Jones et al. |
| 2016/0188936 A1 | 6/2016 | Nunnink et al. |
| 2016/0214715 A1 | 7/2016 | Meffert |
| 2016/0238854 A1 | 8/2016 | Kammans |
| 2016/0274025 A1 | 9/2016 | Skibo et al. |
| 2016/0300336 A1 | 10/2016 | Pacifici |

FOREIGN PATENT DOCUMENTS

| | | |
|---|---|---|
| CA | 2630301 | 6/2007 |
| CA | 2386268 C | 2/2012 |
| CA | 2458123 C | 5/2012 |
| CN | 201575308 | 9/2010 |
| CN | 102261909 | 11/2011 |
| CN | 102829938 | 12/2012 |
| CN | 104457708 | 3/2013 |
| CN | 103364781 | 10/2013 |
| CN | 103528680 | 3/2015 |
| CN | 105300912 | 2/2016 |
| CN | 105300925 | 2/2016 |
| CN | 105761214 | 7/2016 |
| CN | 106199939 | 12/2016 |
| CN | 106236006 | 12/2016 |
| EP | 190280 | 8/1986 |
| EP | 0489546 | 6/1992 |
| EP | 0578129 | 1/1994 |
| GB | 2127537 | 9/1986 |
| GB | 2300325 | 10/1996 |
| GB | 2306828 | 5/1997 |
| GB | 2311852 | 12/1999 |
| GB | 2364840 | 2/2002 |
| JP | H06-301113 | 10/1994 |
| JP | 2004-007413 | 1/2004 |
| JP | 04987360 | 7/2012 |
| JP | 2016-080629 | 5/2016 |
| RU | 2091759 | 9/1997 |
| WO | WO 01/18563 | 3/2001 |
| WO | WO 02/04982 | 1/2002 |
| WO | WO 02/065155 | 8/2002 |
| WO | WO 03/079582 | 9/2003 |
| WO | WO 2006/130734 | 12/2006 |
| WO | WO 2007/081628 | 7/2007 |
| WO | WO 2009/115122 | 9/2009 |
| WO | WO 2009/133414 | 11/2009 |
| WO | WO 2016/029305 | 3/2016 |
| WO | WO 2016/033452 | 3/2016 |
| WO | WO 2016/041079 | 3/2016 |
| WO | WO 2016/076724 | 5/2016 |
| WO | WO 2016/161284 | 10/2016 |

OTHER PUBLICATIONS

International Preliminary Report on Patentability for International (PCT) Patent Application No. PCT/US2016/054161, dated Apr. 12, 2018 9 pages.

Aerius Photonics website, "Aerius NIR/SWIR Illuminators" product sheet, available at www.aeriusphotonics.com/datasheets.html, 2 pages (2009).

"BMW Develops Laser Light for the Car," BMW Corporate Communications Press Release, BMW Group, Sep. 1, 2011, 3 pages.

"Flash LIDAR Technology Shows Promise for Vegetation Canopy Science Measurements," NASA Earth Science and Technology Office, 2009, 2 pages.

"The Infrared & Electro-Optical Systems Handbook: Passive Electro-Optical Systems," Infrared Information Analysis Center, 1993, Stephen B. Campana, Editor, 362 pages (submitted in 2 parts).

Abad et al. "Integrating synthetic objects into real scenes," Computers & Graphics, Feb. 2003, vol. 27, No. 1, pp. 5-17.

Abdalati et al., Report of the Ad-Hoc Science Definition Team for the Ice Cloud and Land Elevation Satellite-II (ICESAT-II), 2008, 69 pages.

Allen et al., "Full-Scale Testing and Platform Stabilization of a Scanning Lidar System for Planetary Landing", Space Exploration Technologies (Wolfgang Fink, ed.), Proceedings of SPIE, vol. 6960, pp. 696004-1-696004-10 (2008).

Allen et al., "Rendezvous Lidar Sensor System for Terminal Rendezvous, Capture, and Berthing to the International Space Station", Sensors and Systems for Space Applications II, SPIE vol. 6958, 8 pages (2008).

Aull et al., "Geiger-Mode Avalanche Photodiodes for Three-Dimensional Imaging", Lincoln Laboratory Journal, vol. 13, No. 2 (2002).

Bakalski et al., "Real Time Processing Enables Fast 3D Imaging at Single Photon Level", Laser Radar Technology and Applications XIII, (Monte D. Turner, Gary W. Kamerman, ed.), Proceedings of the SPIE, vol. 6950, pp. 69500K-1-69500K-9 (2008).

Baker et al., "Advanced Infrared Detectors for Multimode Active and Passive Imaging Applications" Infrared Technologies and Applications XXXIV (Bjorn F. Andresen, Gabor F. Fulop, and Paul R. Norton, ed.), Proceedings of the SPIE, vol. 6940, pp. 69402L-1-69402L-11 (2008).

(56) References Cited

OTHER PUBLICATIONS

Boldt et al., "A Handheld Texel Camera for Acquiring Near-Instantaneous 3D Images," Conference Record of the Forty-First Asilomar Conference on Signals, Systems & Computers, Nov. 4, 2007, pp. 953-957.
Brady et al., "ALHAT System Architecture and Operational Concept", Aerospace Conference, 2007 IEEE, Big Sky, MT, IEEEAC Paper # 1570, Version 4, pp. 1-13 (2007).
Brake "Detection and Measurement of Fugitive Emissions Using Airborne Differential Absorption Lidar (DIAL)," ITT Space Systems Division, Apr. 2006, 11 pages.
Bruneau et al. "Simultaneous measurements of particle backscattering and extinction coefficients and wind velocity by lidar with a Mach-Zehnder interferometer: principle of operation and performance assessment," Applied Optics, Feb. 2003, vol. 42, No. 6, pp. 1101-1114.
Bruneau, "Mach-Zehnder Interferometer as a Spectral Analyzer for Molecular Doppler Wind Lidar", Applied Optics, vol. 40, No. 3, pp. 391-399 (2001).
Chen et al., "RANSAC-Based DARECES: A New Approach to Fast Automatic Registration of Partially Overlapping Range Images", IEEE Transactions on Pattern Analysis and Machine Intelligence, vol. 21, No. 11, 6 pages (Nov. 1999).
Cho et al., "Real-Time 3D Ladar Imaging", 35th Applied Imagery and Patern Recognition Workshop, pp. 5 (2006).
Connes et al., "Astronomical Fourier Spectrometer", Applied Optics, vol. 14, No. 9, pp. 2067-2084 (1975).
Coyle et al., "The High Output Maximum Efficiency Resonator (HOMER) Developed for Long Life, Space-Based Altimetry," IEEE Aerospace Conference, 2006, 7 pages.
Craig et al., "Processing 3D Flash LADAR Point-Clouds in Real-Time for Flight Applications", Sensors and Systems for Space Applications (Richard T. Howard and Robert D. Richards, ed.), Proceedings of SPIE, vol. 6555, pp. 65550D-1-65550D-9 (2007).
De Lafontaine et al., "LAPS: The Development of a Scanning Lidar System with GNC for Autonomous Hazard Avoidance and Precision Landing"; Spaceborne Sensors (Robert D. Habbit, Jr. and Peter Tchoryk, Jr., ed.), Proceedings of SPIE, vol. 5418, pp. 81-93 (2004).
Degnan, "Photon-Counting Multikilohertz Microlaser Altimeters for Airborne and Spaceborne Topographic Measurements", Journal of Geodynamics, vol. 34, pp. 503-549 (2002).
De Jong et al. "IR panoramic alerting sensor concepts and applications," Infrared Technology and Applications XXIX, Proceedings of SPIE vol. 5074, Apr. 2003, pp. 658-668.
Dissly et al., "Flash LIDAR Systems for Planetary Exploration", American Astronomical Society, DPS Meeting, Presentation # 40, Ithaca, NY, Bulletin of the American Astronoimical Society, vol. 41, pp. 560 (2008).
Durrani et al., "Spectral Analysis and Cross-Correlation Techniques for Photon Counting Measurements on Fluid Flows", Applied Optics, vol. 14, No. 3, pp. 778-794 (1975).
Fay et al., "Fusion of Multi-Sensor Pasive and Active 3D Imagery", Enhanced and Synthetic Vision 2001 (Jacques G. Verly, ed.), Proceedings of SPIE, vol. 4363, pp. 219-230 (2001).
Fenton et al., "Simulation Tests of a Lidar-based Spacecraft Pose Determination Algorithm", Sensors and Systems for Space Applications, SPIE vol. 6555, 11 pages (2007).
Fenton, "A LADAR-Based Pose Estimation Algorithm for Determining Relative Motion of a Spacecraft for Autonomous Rendezvous and Dock", Master of Science thesis, Utah State University, 90 pages (2008).
Forkuo et al. "Automatic Fusion of Photogrammetric Imagery and Laser Scanner Point Clouds," Department of Land Surveying & Geo-Informatics, The Hong Kong Polytechnic University, 2005, 6 pages.
Gaudin-Delrieu et al. "The High Resolution Optical Instruments for the Pleiades HR Earth Observation Satellites," International Conference on Space Optics, Oct. 14-17, 2008, Toulouse, France, 7 pages.

Gault, et al., "ERWIN: An E-Region Wind Interferometer", Applied Optics, vol. 35, No. 16, pp. 2913-2922 (1996).
Gentry et al., "The Tropospheric Wind Lidar Technology Experiment (TWiLiTE): An Airborne Direct Detection Doppler Lidar Instrument Development Program", available at www.esto.nasa.gov/conferences/estc2006/papers/b8p2.pdf.
Gillula, "Data Fusion From Multiple Sensors: Real-Time Mapping on an Unmanned Ground Vehicle", 2005 SURF Final Report, California Institute of Technology, 13 pgs (2005).
Goff et al. "Focal Plane AIT Sequence: Evolution From HRG-SPOT 5 to Pleiades HR," Proceedings of the 6th International Conference on Space Optics, ESTEC, Jun. 27-30, 2006, Noordwijk, The Netherlands, 6 pages.
Grund et al. "Simultaneous Profiling of Aerosol Optical Properties, Gas Chemistry, and Winds with Optical Autocovariance Lidar", Paper 1 of 2 presented at the 24th International Laser Radar Conference, Jun. 23-27, 2008, 5 pages.
Grund et al. "Enabling Characteristics of Optical Autocovariance Lidar for Global Wind and Aerosol Profiling", AGU, American Geophysical Union, Fall Meeting, San Francisco, CA (Dec. 16, 2008).
Grund et al., "Optical Autocovariance Wind Lidar (OAWL) for Efficient Space-Based Direct-Detection High-Resolution Aerosol Backscatter Winds", Paper 2 of 2 presented at the 24th International Laser Radar Conference, Jun. 23-27, 2008, 5 pages.
Grund et al., "Optical Autocovariance Wind Lidar and Performance from LEO", 14th Coherent Laser Radar Conference, Snowmass, CO (Jul. 7, 2007).
Grund et al., "Supporting NOAA and NASA High-Performance Space-Based DWL Measurement Objectives with a Minimum Cost, Mass, Power, and Risk Approach Employing Optical Autocovariance Wind Lidar (OAWL)", Space Winds Lidar Working Group, Monterrey, CA (Feb. 6, 2008).
Grund et al., Poster Entitled "Optical Autocovariance Wind Lidar (OAWL) for Efficient Space-Based Direct-Detection High-Resolution Aerosol Backscatter Winds", presented at the Coherent Laser Radar Conference, Jul. 2007, presented at the Working Group on Space-based Lidar Winds, Feb. 2008, and presented at the International Laser Radar Conference, Boulder, CO, Jun. 23-27, 2008, 1 page.
Grund et al., Presentation Entitled "Optical Autocovariance Wind Lidar and Performance from LEO", presented at the Coherent Laser Radar Conference, Jul. 11, 2007, 30 pages.
Grund et al., Presentation Entitled "Simultaneous Profiling of Aerosol Optical Properties, Gas Chemistry, and Winds with Optical Autocovariance Lidar", 24th ILRC Conference (Jun. 23, 2008).
Grund, "An Alternative Direct Detection Approach to Doppler Winds that is Independent of Aerosol Mixing Ratio and Transmitter Frequency Jitter", Space Winds Lidar Working Group, Miami, FL (Feb. 8, 2007).
Grund, "Lidar Wind Profiling from Geostationary Orbit Using Imaging Optical Autocovariance Interferometry", Space Winds Lidar Working Group, Snowmass, CO (Jul. 17, 2007).
Grund, Christian J., Power Point Presentation Entitled "Optical Autocovariance: Alternative Direct Detection Approach to Doppler Winds that is Independent of Aerosol Mixing Ratio and Transmitter Frequency Jitter", presented at the Working Group Conference on Space-Based Lidar Winds, Feb. 6-9, 2007, 12 pages.
Habbit et al., "Utilization of Flash LADAR for Cooperative and Uncooperative Rendezvous and Capture", Space Systems Technology and Operations (Peter Tchoryk, Jr. and James Shoemaker, ed.), Proceedings of SPIE, vol. 5088, pp. 146-157 (2003).
Hancock et al. "Shallow-Depth 3D Interaction: Design and Evaluation of One-, Two- and Three-Thouch Techniques," CHI 2007 Proceedings, Apr. 28-May 3, 2007, San Jose, CA, USA, pp. 1147-1156.
Hyde et al., "Mapping Forest Structure for Wildlife Habitat Analysis Using Multi-Sensor (LiDAR, SAR/InSAR, ETM+, Quickbird) Synergy", Remote Sensing of Environment, vol. 102, pp. 63-73 (2006).
Jacquinot, "The Luminosity of Spectrometers with Prisms, Gratings, or Fabry-Perot Etalons", Journal of the Optical Society of America, vol. 44, No. 10, pp. 761-765 (1954).

(56) References Cited

OTHER PUBLICATIONS

Jasiobedzki et al., "Autonomous Satellite Rendezvous and Docking Using LIDAR and Model Based Vision", Spaceborne Sensors II, SPIE vol. 5798, 12 pages (2005).
Kasten, et al., "Fabrication and Characterization of Individually Addressable Vertical-Cavity Surface-Emitting Laser Arrays and Integrated VCSEL/PIN Detector Arrays", Proceedings of SPIE, vol. 6484, 64840C, 2007.
Kumar et al., "Determination of the Instrument Function of a Grating Spectrometer by Using White-Light Interferometry", Applied Optics, vol. 36, No. 19, pp. 4535-4539 (1997).
Lamoreux et al., "Relative Navigation Sensor for Autonomous Rendezvous and Docking", Laser Radar Technology and Applications VIII (Gary W. Kamerman, ed.), Proceedings of the SPIE, vol. 5086, pp. 317-328 (2003).
Ledebuhr et al., "Micro-Satellite Ground Test Vehicle for Proximity and Docking Operations Development," Aerospace Conference, Mar. 10-17, 2001, IEEE Proceedings, Jan. 1, 2001, vol. 5, pp. 2493-2504.
Lefsky et al., "Estimates of Forest Canopy Height and Aboveground Biomass Using ICESat", Geophysical Research Letters, vol. 32, L2202, 4 pages (2005).
Lenz et al. "Flight Testing of an Advanced Airborne Natural Gas Leak Detection system," ITT Industries Space Systems, LLC, Oct. 2005, 84 pages.
Lieber et al., "Development of a Validated End-to-End Model for Space-Based Lidar Systems", Lidar Remote Sensing for Environmental Monitoring VIII (Singh, Upendra N. ed.), Proceedings of the SPIE, vol. 6681, 66810F (2007).
Lieber et al., "Integrated System Modeling for Evaluating the Coronagraph Approach to Plant Detection", High-Contrast Imaging for Exo-Planet Detection (Schultz, Alfred B. ed.), Proceedings of the SPIE, vol. 4860 (2002). (Abstract only).
Lieber, Mike et al., "System Verification of the JMEX Mission Residual Motion Requirements with Integrated Modeling", UV/Optical/IR Space Telescopes: Innovative Technologies and Concepts II (MacEwen, Howard A. ed.), Proceedings of the SPIE, vol. 5899, 589901, pp. 1-12 (2005).
Marino et al., "Jigsaw: A Foliage-Penetrating 3D Imaging Laser Radar System"; Lincoln Laboratory Journal, vol. 15, No. 1, pp. 23-36 (2005).
Mayo, Jr., "Photon Counting Processor for Laser Velocimetry", Applied Optics, vol. 16, No. 5, pp. 1157-1162 (1977).
Morton, "Photon Counting", Applied Optics, vol. 7, No. 1, pp. 1-10 (1968).
Oberle et al., "Toward High Resolution, Ladar-Quality 3-D World Models Using Ladar-Stereo Data Integration and Fusion," Army Research Laboratory, ARL-TR-3407, 37 pgs (2005).
Pack et al., "A Co-Boresighted Synchronized Ladar/EO Imager for Creating 3D Images of Dynamic Scences", Laser Radar Technology and Applications, X (Gary W. Kamerman, ed.), Proceedings of SPIE, vol. 5791, pp. 42-50 (2005).
Pierrottet et al., "Characterization of 3-D Imaging Lidar for Hazard Avoidance and Autonomous Landing on the Moon"; Laser Radar Technology and Applications XII (Monte D. Turner and Gary W. Kamerman, ed.), Proceedings of SPIE, vol. 6550, pp. 655008-1-655008-9 (2007).
Pranyies et al. "SiC Focal Plane Assembly for the PLEIADES HR Satellite," Sensosrs, Systems, and Next-Generation Satellites VIIIL, Proceedings of SPIE vol. 5570, Sep. 13, 2004, pp. 568-576.
Rabinovich et al., "45 Mbps Cat's Eye Modulating Retro-Reflector Link Over 7 Km", Free-Space Laser Communications VI, Proceedings of the SPIE, vol. 6304, pp. 63040Q (2006). (Abstract only).
Richardson et al., "Design and Performance Considerations of Cat's Eye Retroreflectors for Use in Open-Path Fourier-Transform-Infrared Spectrometry", Applied Optics, vol. 41, No. 30, pp. 6332-6340 (2002).
Ring et al., "Field-Compensated Michelson Spectrometers", Applied Optics, vol. 11, No. 3, pp. 507-516 (1972).
Riris et al., "The Lunar Orbiter Laser Altimeter (LOLA) on NASA's Lunar Reconnaissance Orbirot (LRO) Mission", Sensors and Systems for Space Applications (Richard T. Howard and Robert D. Richards, ed.), Proceedings of SPIE, vol. 6555, pp. 655501-1-655501-8 (2007).
Roberts, Jr. et al., "Aperture Sharing Between Low-Background Infrared Sensors and Ladar Sensors", Aerospace Applications Conference, Proceedings of the IEEE, vol. 4, pp. 495-508 (1996).
Ronnholm et al. "Integration of Laser Scanning and Photogrammetry," Proceedings of the ISPRS Workshop on Laser Scanning 2007 and SilviLaser 2007, Sep. 2007, vol. 36, Part 3, pp. 355-362.
Ruel et al., "Field Testing of a 3D Automatic Target Recognition and Pose Estimation Algorithm", Automatic Target Recognition XIV, SPIE vol. 5426, 10 pages (2004).
Ruel et al., "Real-Time 3D Vision Solution for On-Orbit Autonomous Rendezvous & Docking", Spaceborne Sensors III, SPIE 6220, 11 pages (2006).
Scherello "State of the art methane leak detection CHARM® and GasCam®," Open Grid Europe, Oct. 2011, 33 pages.
Shepherd et al., "WAMDII: Wide-Angle Michelson Doppler Imaging Interferometer for Spacelab", Applied Optics, vol. 24, No. 11, pp. 1571-1584 (1985).
Shepherd et al., "WINDII—The Wind Imaging Interferometer for the Upper Atmosphere Research Satellite", Geophys. Res. vol. 98, No. D6, pp. 10,725-10,750 (1993).
Shugart et al., "Determination of Stand Properties in Boreal and Temperate Forests Using High-Resolution Imagery," Forest Science, 2000, vol. 46, No. 4, pp. 478-486.
Smith et al., "Diffractive Optics for Moon Topography Mapping"; Micro (MEMS) and Nanotechnologies for Space Applications (Thomas George and Zhong-Yang Cheng, ed.), Proceedings of SPIE, vol. 6223, pp. 622304-1-622304-10 (2006).
Stentz et al., "Real-Time, Multi-Perspective Perception for Unmanned Ground Vehicles", Proceedings of the Association for Unmanned Vehicle Systems International, 15 pgs (2003).
Stettner et al., "Three Dimensional Flash Ladar Focal Planes and Time Dependent Imaging," International Symposium on spectral Sensing Research, May 31, 2006, retrieved at www.advancedscientific-concepts.com/technology/documents/ThreeDimensionalFlashLabdarFocalPlanes-ISSSRPaper.pdf, 5 pages.
Tan et al., "Design and Performance of a Multiwavelength Airborne Polarimetric Lidar for Vegetation Remote Sensing"; Journal of Applied Optics, vol. 43, No. 11, pp. 2360-2368 (2004).
Trenkle et al., "3D Sensor Algorithms for Spacecraft Pose Determination", Spaceborne Sensors III (Richard T Howard and Robert D. Richards, ed.), Proceedings of SPIE, vol. 6220, pp. 62200D-1-62200D-14 (2006).
Vallerga et al., "Noiseless, High Frame Rate (>KHz), Photon Counting Arrays for Use in the Optical to the Extreme UV", University of California, Berkeley—Sciences Laboratory and University of Geneva, Switzerland, available at www.ssl.berkeley.edu/~mcphate/AO/ao_medipix.html (2004-present).
Vasile et al., "Pose-Independent Automatic Target Detection and Recognition Using 3D Laser Radar Imagery", Lincoln Laboratory Journal, vol. 15, No. 1, 18 pages (2005).
Wang et al., "Optimized Reflective Wide-Angle Michelson Phase-Stepping Interferometer", Applied Optics, vol. 39, No. 28, pp. 5147-5160, (2000).
Weimer et al., "Seeing the Forest and the Trees: An electronically steerable flash LiDAR improves vegetation studies," Earth Imaging Journal, 2009, pp. 33-34.
Weinberg et al., "Flash Lidar Systems for Hazard Detection, Surface Navigation and Autonomous Rendezvous and Docking", 2007 LEAG Workshop on Enabling Exploration, 2 pgs (2007).
Weishampel et al., "Semivariograms from a forest transect gap model compared with remotely sensed data," Journal of Vegetation Science, 1992, vol. 3, Iss. 4, pp. 521-523 (Abstract only).
Wikipedia, "RANSAC", available at http://en.wikipedia.org/wiki/RANSAC, 5 pages (2009).
Xun et al., "Expanding range of pulsed range sensors with active projection from spatial light modulators", Spaceborne Sensors III, Proc. of SPIE vol. 6220, 62200I, 2006, 9 pages.

(56) References Cited

OTHER PUBLICATIONS

Yoon et al., "High Frequency Attitude Motion of ICESat", Advances in Astronautical Sciences (David A. Vollado, Michael J. Gabor and Prasun N. Desai ed.), vol. 120: Spaceflight Mechanics, Part 1, pp. 117-131 (2005).
International Search Report and Written Opinion for International (PCT) Patent Application No. PCT/US2016/054161, dated Dec. 9, 2016 10 pages.

* cited by examiner

DIFFERENTIAL ABSORPTION LIDAR

CROSS REFERENCE TO RELATED APPLICATIONS

This application claims the benefit of U.S. Provisional Patent Application Ser. No. 62/233,768, filed Sep. 28, 2015, the entire disclosure of which is hereby incorporated herein by reference.

FIELD

Systems and methods for remotely monitoring gas emissions are provided.

BACKGROUND

The detection of greenhouse gas emissions has become an important part of ensuring the efficient operation of various systems, and compliance with environmental regulations. For example, remote leak detection from an aircraft or spacecraft platform is essential for efficiently monitoring manufacturing zones, agricultural areas, pipeline systems, drilling operations, and the like. In addition to simple leak detection, it is desirable to provide information regarding the magnitude of a detected leak, and the precise location of the leak. Also, it is desirable to provide such information quickly and conveniently.

One way of obtaining information regarding the amount of atmospheric trace gases is to sense the spectral absorption of reflected sunlight. In particular, the amount of absorption of light at wavelengths corresponding to the spectral lines of the gas of interest can be detected and measured. In general, the higher the absorption of light at such wavelengths, the higher the concentration of the associated gas in the portion of the atmosphere from which the sampled light was collected. Similarly, the absorption of thermal emissions by atmospheric trace gases can be measured to obtain information regarding the amount of such gases. Various spectrometers have been developed for enabling such measurements. For example, Fourier transform spectrometers have been developed that are capable of high spectral resolution. However, such instruments are relatively large and complex. Other instruments for sensing light within a narrow range of wavelengths include devices utilizing optical cavities, such as Fabry-Perot interferometers and multiple cavity filters formed from thin films. However, the sensitivity and signal to noise ratio of such devices has been limited.

One approach to providing a filter having characteristics precisely correlated to the gas being sensed is to provide a cell containing a sample of the gas of interest. By comparing the difference between the light passed through the gas-containing cell to a detector, and light received at a detector that has not been passed through the cell, information regarding the presence of that gas in the atmosphere can be obtained. Although systems using samples of the gas being sensed are capable of providing filter characteristics that are correlated to that gas, they are difficult to implement.

Another approach is to known as a Differential Absorption Lidar (DIAL). In a DIAL system, on line and off line pulses of light are directed towards an area of interest. The on line light has a wavelength that coincides with an absorption line of a gas of interest. The off line wavelength is selected so that it is substantially less affected or unaffected by the gas of interest. By comparing an intensity of light of the first wavelength that has been reflected from the area of interest to the intensity of light of the second wavelength that has been reflected from the area of interest, an estimated amount of the gas of interest that the light has passed through can be determined. In previous DIAL systems, cavity seeding and locking has been used to control laser wavelength and linewidth. However, such systems do not achieve desired levels of laser beam combining and energy profile matching. In addition, previous implementations of DIAL systems have been expensive and complex to implement. Furthermore, previous DIAL systems do not accomplish both gas sensing and 3D topographical imaging simultaneously. Accordingly, previous implementations of these systems have required multiple passes over the area of interest.

In some previous instruments, a 3D imaging system is used in combination with a separate methane sensing system. As another example, a system performs data fusion with respect to data from multiple image sensors and data from a differential absorption LIDAR carried by an aircraft. The method of acquiring data using such a system includes the steps of: (a) turning ON a DIAL sensor to detect a target of interest during a first flight pass over a region of interest (ROI), wherein the target of interest is a gas or oil pipeline leak; (b) detecting the target of interest using the DIAL sensor; and (c) storing location of the detected target in a look up table (LUT). The method also includes the steps of: (d) during a second flight pass over the ROI, triggering another sensor to turn ON at or about the location stored in the LUT; and (e) confirming presence of the target of interest using both ON-sensors. If necessary, a third flight pass over the ROI is conducted and yet another sensor is triggered to turn ON at or about the location stored in the LUT. Presence of the target of interest is confirmed using all three ON-sensors. Accordingly, such systems require multiple passes over an area of interest.

SUMMARY

Embodiments of the present disclosure provide an advanced Differential Absorption Lidar (DIAL) instrument or system for measuring gas concentration remotely. In at least some embodiments, a unique DIAL system is provided. The DIAL system operates by using pulses that are both on-line and off-line of a targeted molecular absorption feature. The DIAL system uses Volume Bragg Gratings (VBGs) for laser wavelength and linewidth control. In accordance with further embodiments of the present disclosure, the system incorporates polarization combining, polarization circularization, reference pick-off, and fiber coupling. These provisions can help ensure that the on-line and off-line beams interact with the target in like manner.

In accordance with still further embodiments of the present disclosure, the DIAL system may be configured as a flash DIAL system. The flash DIAL invention incorporates a multiple pixel sensor array. In operation, the flash DIAL system can simultaneously combine topography (3D imaging) and gas detection in an integrated single sensor. This can improve spatial resolution and chemical sensitivity at reduced size, weight, and power (SWaP) as compared to alternative systems. The flash LIDAR topographic modality uses a single pulse to illuminate a whole scene imaged onto a focal plane array. The flash LIDAR focal plane array observes a pulse waveform from each pixel, giving the capability to calculate pulse time of flight and therefore distance at each pixel. Embodiments of the present disclosure use the same waveform capture at each pixel to capture DIAL information by using pulses that are both on-line and off-line of a targeted molecular absorption feature.

DETAILED DESCRIPTION

Figure 1:
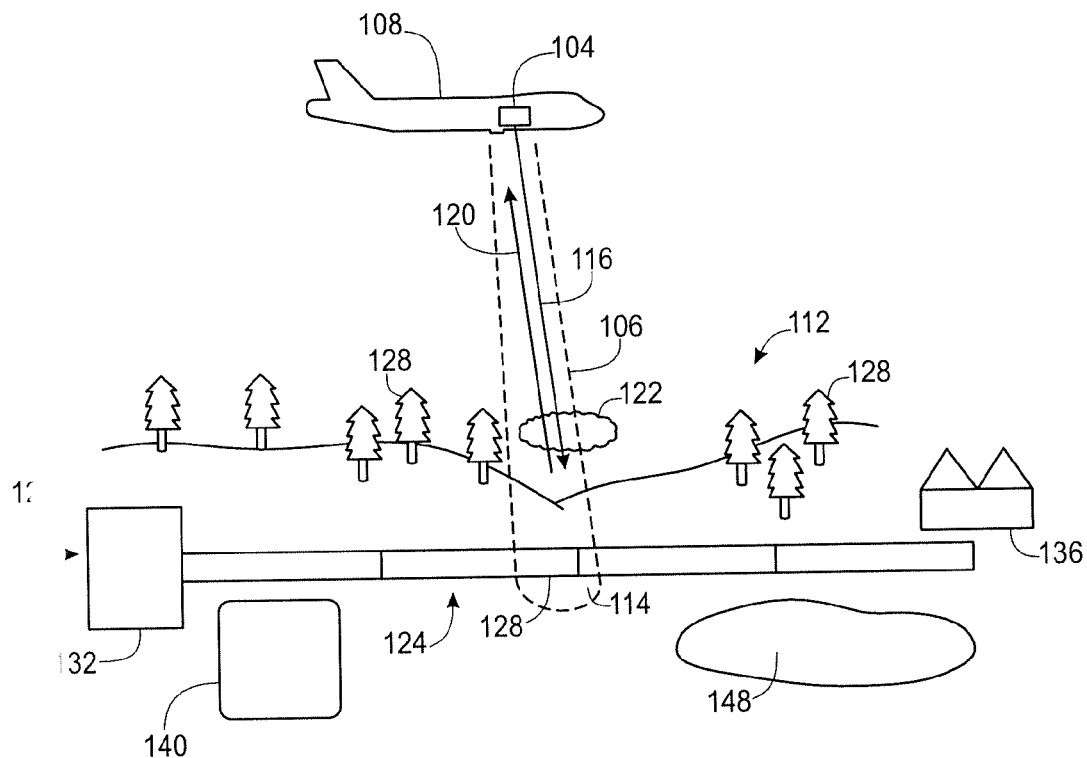
FIG. 1 depicts an arrangement for sensing gas emissions in accordance with embodiments of the present disclosure.

A remote sensor system or a light detection and ranging (LIDAR) system 104 in accordance with embodiments of the present invention, in an exemplary operating environment, is depicted in FIG. 1. The LIDAR system 104, also referred to herein as a sensor system 104, is mounted to a platform 108. In this example, the platform 108 is an airplane, however, other mobile or even stationary platforms 108 may be associated with the LIDAR system 104. Examples of other mobile platforms 108 include satellites, helicopters, unmanned aerial vehicles, autonomous rovers, balloons, cars, all-terrain vehicles, ships or other mobile platforms. Examples of stationary platforms 108 include radio towers, power transmission towers, observation towers, telephone poles, or other stationery supports. In general, the platform 108 is used to place the sensor system 104 in a location from which a survey area, target region, or scene 112 is observed. When the sensor system 104 is in a desired position with respect to the scene 112, it is operated to output illumination light 116 and pass the light through a target volume 106 to illuminate a target area or areas 114 within the scene 112. Reflected light 120 is returned from the target area 114 with the scene 112, and is detected by the LIDAR or sensor system 104. Information regarding the time of flight of the light is used to obtain range information between the sensor system 104 and the target area 114 within the scene 112. Information regarding the amplitude of the reflected light 120 is used to obtain information regarding the concentration of a gas of interest 122 within the target volume 106. The scene 112 can include a man made facility 124 or a natural feature under inspection or monitoring. Examples of a facility, structure, or area 124 that can be inspected or monitored using a sensor system 104 as disclosed herein include pipelines 128, wellheads 132, factories 136, agricultural zones 140, or the like.

As can be appreciated by one of skill in the art after consideration of the present disclosure, different target areas 114 comprising different elements or features within a scene 112 will reflect the illumination light 116 differently. For example, a terrain feature comprising a forested hillside 128 may reflect the illumination light 116 less efficiently than a lake or pond 148. As a further example, an area within the scene 112 covered by snow will typically reflect the illumination light 116 more efficiently than an area that is not covered by snow. Accordingly, as discussed in greater detail elsewhere herein, the sensor system 104 may comprise a differential absorption LIDAR (DIAL) system that corrects for the reflectivity of surfaces within a target area 114.

As can also be appreciated by one of skill in the art after consideration of the present disclosure, information regarding the location at which an emission of a gas of interest to 122 is detected is important to efficiently addressing a potential leak or other unauthorized emission. Accordingly, at least some embodiments of the present disclosure can include a two-dimensional context camera. Still other embodiments of the present disclosure can additionally or alternatively include a three dimensional imaging type sensor that is used in connection with detecting the reflected light 120.

Figure 2:
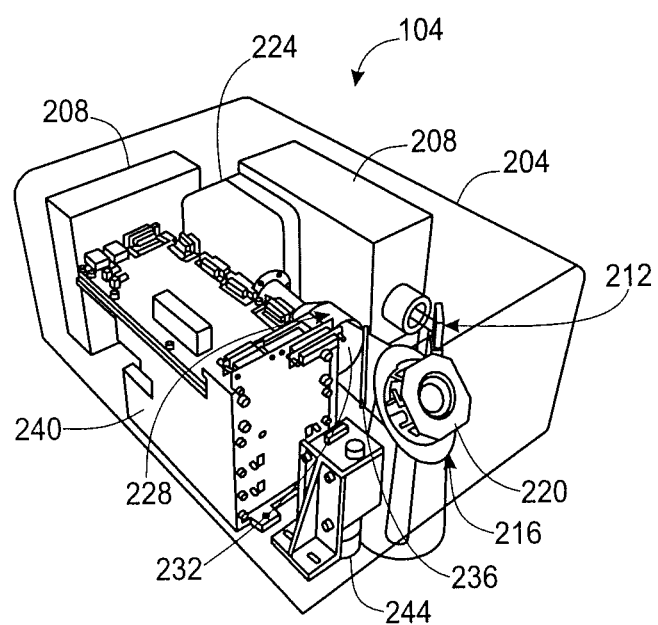
FIG. 2 depicts a sensor system in accordance with embodiments of the present disclosure.

FIG. 2 depicts a sensor system 104 accordance with embodiments of the present disclosure. In general, the sensor system 104 features a shared enclosure or frame 204 that carries or encloses various components of the system 104. These components can include a plurality of light source assemblies 208, a beam coupling assembly 212, and transmit optics 216. The transmit optics 216 can include a wide-angle steering mirror 220. Alternatively or in addition, the transmit optics 216 can be mounted to a gimbal, to allow the field of view to be pointed at a target area 114. In accordance with still other embodiments of the present disclosure, the entire sensor system 104, or selected portions of the sensor system 104, can be mounted to a gimbal. The components of the system 104 can additionally include a detector 224, such as a single pixel detector or a multiple pixel array detector. The detector 224 can be associated with an imaging lens or a receive telescope 228, which can include an infrared lens 232. In accordance with at least some embodiments of the present invention, the transmit optics 216 and the receive telescope 228 can share the steering mirror 220. In such embodiments, a mirror or a beam splitter/combiner 236 can be provided to direct light between the steering mirror 220, the transmit optics 216, and the receive optics 228. The enclosure 204 can additionally house electronics 240, such as processors, driver circuits, memory, communications devices, and the like, and a context camera 244, as discussed in greater detail elsewhere herein.

Figure 3:
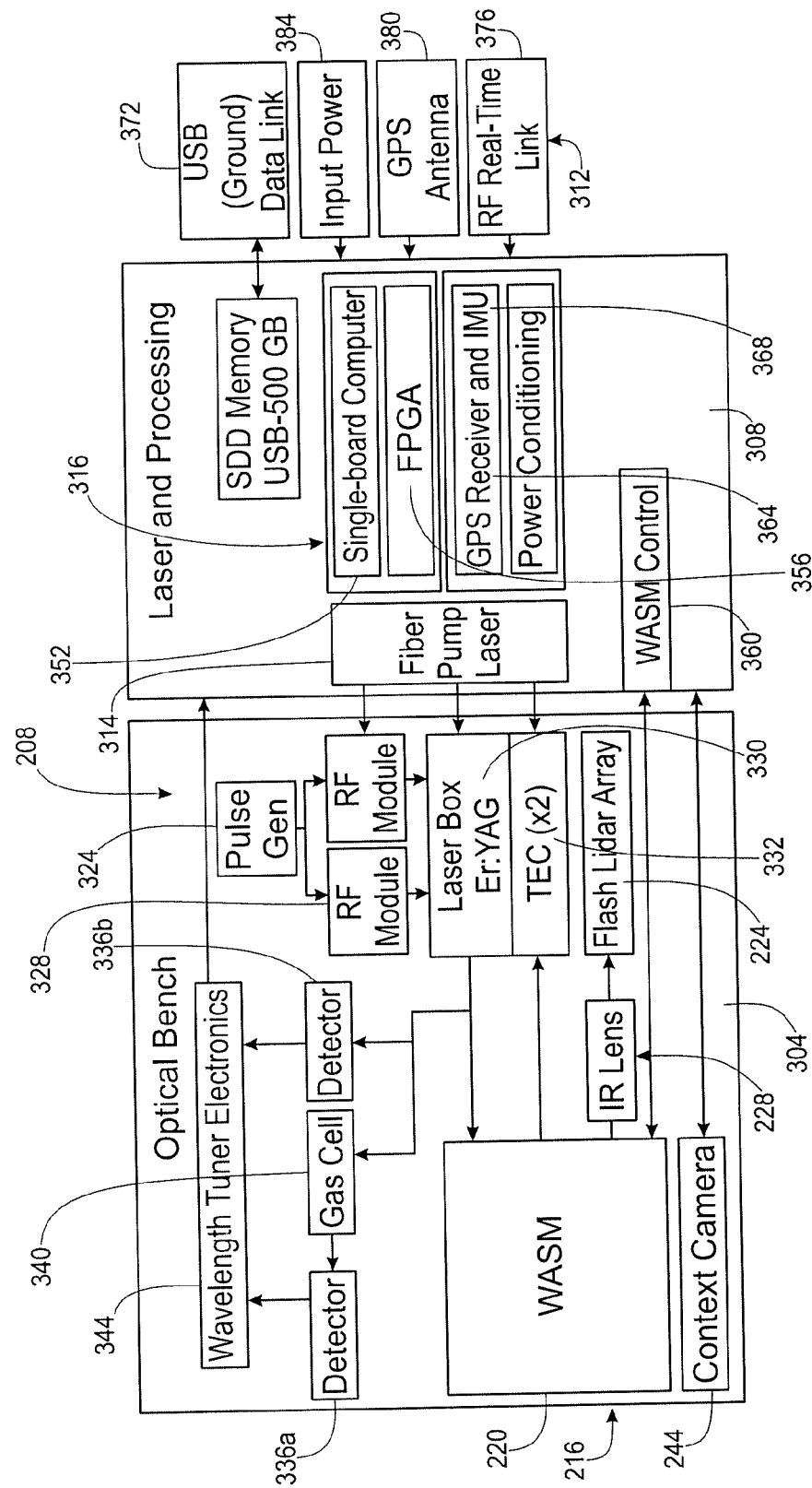
FIG. 3 is a block diagram depicting components of a sensor system in accordance with embodiments of the present disclosure.

FIG. 3 is a block diagram depicting components of a sensor system 104 in accordance with embodiments of the present disclosure. In this functional depiction, the components of the sensor system 104 can generally be divided into those that are part of an optical bench 304, part of a light source and processing section 308, or associated with input/output functions 312. The optical bench 304 generally includes components that direct illumination light 116 from the light source assemblies 208 towards the target area 114, and that ensure the light 116 is provided at a desired wavelength, linewidth, and pulse duration. The light source and processing section 308 generally includes one or more light sources or lasers 314, signal processing and control components 316 provided as part of the electronics 240, and positioning, control, and power components 320. The components associated with input/output functions 312 can include, as examples and without limitation, communications transmitters and receivers, positioning system receivers, and connections to power sources.

The components included in the optical bench 304 more particularly include pulse generation 324 and radio frequency module 328 components that interact with one or more laser boxes or cavities 330 and thermoelectric controllers 332 to control the output wavelength of laser pulses as transmitted light 116. The optical bench 304 can further include components for monitoring the output of the light from a cavity 330. These monitoring components can include detectors 336, at least one of which is associated with a gas cell 340, and wavelength tuner electronics 344 that can operate to provide a feedback signal to the electronics 344. Still other components that can be included as part of the optical bench 304 include the steering mirror 220, which can be implemented as a wide-angle steering mirror, the context camera 244, the detector 224, and an imaging lens or receive telescope 228 that directs light received at the steering mirror 220 as reflected light 120 to the detector 224.

The components included in the positioning, control, and power components section 320 can more particularly include a single board computer 352 and/or a field programmable gate array 356, or other processing components as part of the processing and control components 316 of the electronics 240. The processing and control components 316 generally operate to control the production of light having desired characteristics at desired times, determining the time of flight of light signals, and determining the amplitude of received light. Other functions performed by the processing and control components 316 can include correlating signals received from a target area 114 to a geographic location, determining a concentration of a gas of interest 122 within a target volume 106, storing data generated by the sensor system 104, transmitting data, receiving and implementing control commands, correlating three-dimensional sensor information with topographic maps, correlating three-dimensional sensor information with information from a two-dimensional context camera 244, or the like. In accordance with at least some embodiments, a dedicated steering mirror control section 360 can be provided. As can be appreciated by one of skill in the art after consideration of the present disclosure, the steering mirror control section 360 can include processors, memory, and drivers for controlling operation of the steering mirror 220, and in particular in controlling the volume of interest 106 encompassed by the field of view of the sensor system 104. Other components that can be included in the positioning, control, and power components section 320 include a global positioning system (GPS) receiver 364. In addition, an inertial measurement unit 368 can be included.

The components associated with the input/output functions 312 can, more particularly, include data links such as a ground datalink 372 and a radio frequency datalink 376 to support the real time transmission of data. As can be appreciated by one skill in the art after consideration of the present disclosure, data links 372 or 376 can output information obtained by the sensor system 104 to a remote or separate system or user. Other input/output components can include a GPS antenna 380, and connections to one or more power supplies 384.

Figure 4:
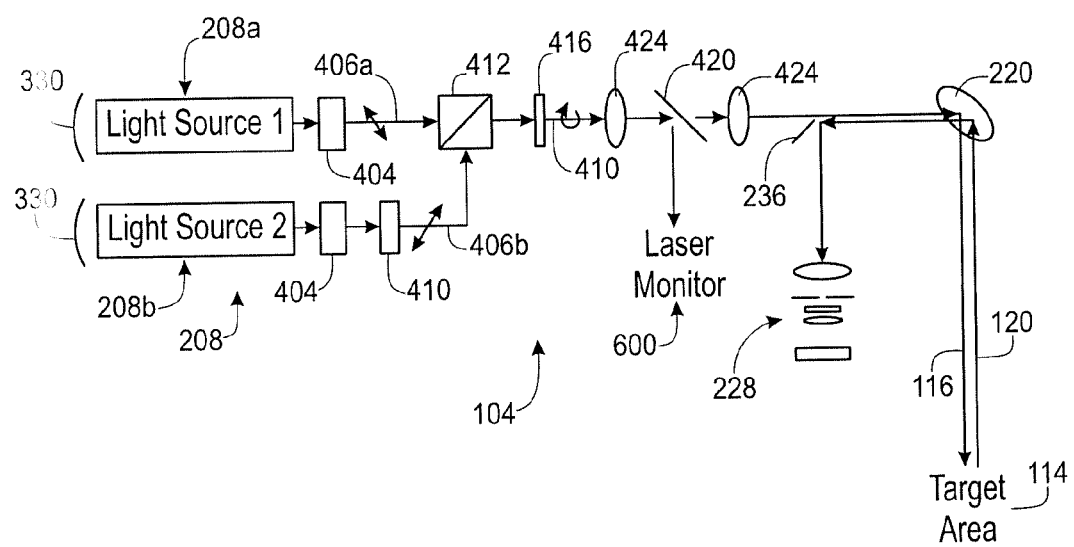
FIG. 4 is a schematic depiction of components of a sensor system in accordance with embodiments of the present disclosure.

FIG. 4 is a schematic depiction of components of a sensor system 104 in accordance with embodiments of the present disclosure. In particular, this view of the sensor system 104 depicts components of the light source assemblies 208 and beam forming components. As shown in the figure, the sensor system 104 can include multiple light source assemblies 208. Each light source assembly 208 can include a light source 314, such as a laser. As an example, but without limitation, the laser light source 314 can include a YAG laser. In addition, each light source assembly 208 can include a laser box or cavity 330. In accordance with embodiments of the present disclosure, the laser cavity 330 can include or be associated with a volume Bragg grating (VBG) 404 as an output coupler. As can be appreciated by one of skill in the art after consideration of the present disclosure, the VBG 404 of a laser source 208 functions to select the wavelength that is output by the laser source 208. Moreover, the operation of VBG 404 in this context is very reliable.

In accordance with embodiments of the present disclosure, the light 406a output by a first one of the light source assemblies 208a is selected to have a wavelength (a first wavelength) that is absorbed by a gas of interest 122, while the light output by a second one of the light source assemblies 208b is selected to have a wavelength (a second wavelength) that is not significantly absorbed by the gas of interest 122. Moreover, the first wavelength can be selected to be a wavelength other than the wavelength at which maximum absorption by the gas of interest 122 is observed, to increase the amount of light within the wavelength that is reflected back to the sensor system 104 when the gas of interest 122 is present within the target volume. The second wavelength can be selected to be a wavelength that experiences similar rates of absorption as the first wavelength by known or expected constituent gases within the ambient environment encompassing the target volume 106.

In accordance with still further embodiments of the present disclosure, the first light source assembly 208a is configured to output light 406a having a first linear polarization, while the second light source assembly 208b is configured to output light 406b having a second linear polarization that is orthogonal to the first polarization. The second light source assembly 208b can include or be associated with a ½ wave plate 410 to impose the second polarization on the output light 408b. The light 406 output by the light source assemblies 208 is placed along a common transmission path 408 by a polarization beam combiner 412. A quarter wave plate 416 is located along the common transmission path 408, and functions to transform the polarization of the light 406 from the light source assemblies 208 into circularly polarized light 410. As can be appreciated by one of skill in the art after consideration of the present disclosure, by transforming the polarization of the light 406 from the light sources 208 into a circular polarization, the interaction of light from both light sources 208 with surfaces within the target area 114 will be similar.

A pickoff mirror 420 is located along the path of the circularly polarized light 410. The pickoff mirror 420 directs a portion of the light to a laser monitor assembly 600, discussed elsewhere herein. The portion of the light not redirected to the laser monitor assembly 600 by the pickoff mirror 420 passes through the beam splitter/combiner 236 to the steering mirror 220, which directs that light to the target area 114 as the transmitted beam 116. In accordance with embodiments of the present disclosure, an objective lens or lens assembly 424 can be provided between the quarter wave plate 416 and the pick off mirror 420, or between the pick off mirror 420 and the steering mirror 220.

The light 120 reflected from the target area 114 is received by the sensor system 104, and is directed by the steering mirror 220 to the mirror 236, and through the receive telescope 228, to the detector 224. The receive telescope 228 may be a reflecting telescope, including off-axis or cassegrain primary reflectors and fold mirrors, a field-stop, focusing lenses and filters, as appropriate to manage the placement of light onto the detector 224. Alternatively, the receive telescope 228 may be a refracting set of objective lenses with stops and filters as appropriate. In accordance with embodiments of the present disclosure, the detector 224 may comprise a single pixel detector. In accordance with still other embodiments of the present disclosure, the detector 224 may comprise a multiple pixel detector, such as a two-dimensional array detector, for example where the sensor system 104 incorporates a flash LIDAR sensor. The detector 224 operates to detect a time of arrival and an amplitude of received light. As an example, a detector 224 may comprise a 10 bit single pixel detector. As another example, a detector 224 may comprise a 10 bit detector with a 128 by 128, or other two dimensional array of pixels (i.e. the detector 224 may comprise an imaging detector to implement a flash LIDAR system). The receive telescope 228 can operate to focus the received light 120 onto the detector 224.

Figure 5:
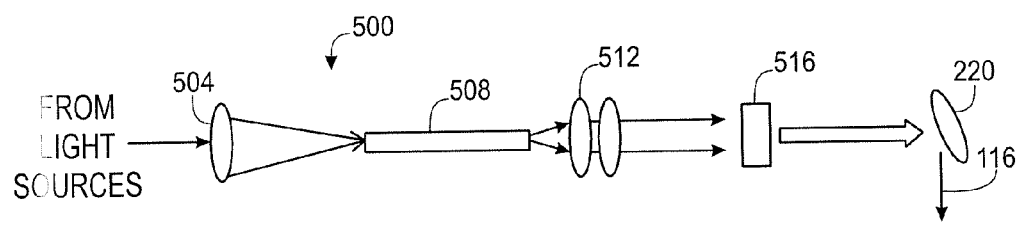
FIG. 5 is a schematic depiction of a beam coupling assembly in accordance with embodiments of the present disclosure.

FIG. 5 is a schematic depiction of a beam coupling assembly 500 in accordance with embodiments of the present disclosure. The beam coupling assembly 500 can be located between the light sources 208 and the steering mirror 220, and can be provided as part of or in association with the transmit optics 216. In accordance with embodiments of the present disclosure, each light source assembly 208 may include or be associated with a beam coupling assembly 500. In accordance with other embodiments of the present disclosure, the beam coupling assembly 500 can be located along a common transmission path 408 or 410, in which case the light source assemblies 208 share a common beam coupling assembly 500. The beam coupling assembly 500 generally includes a lens or lens assembly 504 that directs light from a laser source 208 onto a multimode fiber 508. A collimator 512 is located so as to receive light from the multimode fiber 508. The collimated light is then passed through a diffuser 516, and from there to the steering mirror 220. As can be appreciated by one of skill in the art after consideration of the present disclosure, this arrangement can have the advantage of reducing speckle in the transmitted light 116.

Figure 6:
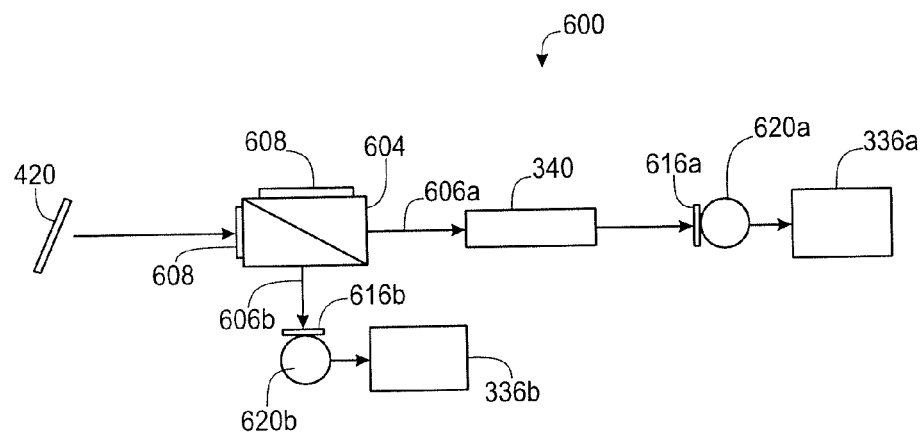
FIG. 6 is a schematic depiction of a laser monitor assembly in accordance with embodiments of the present disclosure.

FIG. 6 is a schematic depiction of a laser monitor assembly 600 in accordance with embodiments of the present disclosure. In accordance with embodiments of the present disclosure, the laser monitor assembly 600 includes a non-polarizing beam splitter 604. The non-polarizing beam splitter 604 can direct half of the light received from the pickoff mirror 420 along a first path 606a, and can direct the other half of the light along a second path 606b. Absorbers 608 can be included to prevent cross talk between the two paths 606a and 606b. Light directed along the first path 606a is received at a gas cell 340. In accordance with embodiments of the present disclosure, the gas cell 340 contains a sample of the gas of interest 122. Light exiting the gas cell 340 is provided to a first diffuser 616a and then to a first integrating sphere 620a. A first detector 336a is positioned to receive light exiting the first integrating sphere 620a. Light directed along the second path 606b is provided to a second diffuser 616b and a second integrating sphere 620b, and then to a second detector 336b. The configuration of a laser monitor assembly provided by embodiments of the present disclosure ensures even illumination of the detectors 336a and 336b, even in the presence of vibration, for example from a platform 108 carrying the sensor system 104. Moreover, as can be appreciated by one of skill in the art after consideration of the present disclosure, the laser monitor assembly 600 verifies the wavelengths and energy content of the light produced by the light source assemblies 208, and allows computation of the effective absorption cross section of the reference gas 340.

Figure 7:
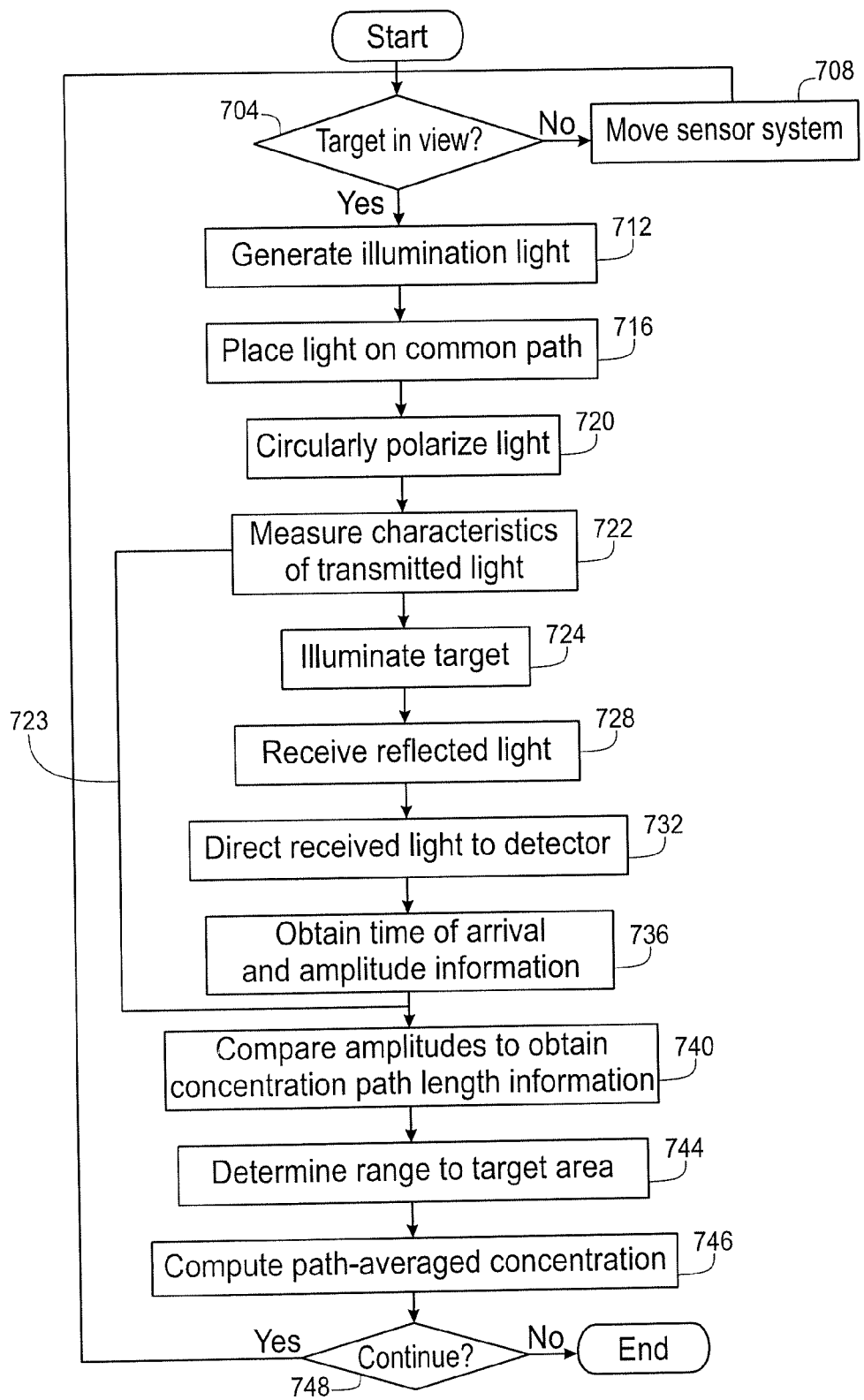
FIG. 7 is a block diagram depicting aspects of a method for sensing gas emissions in accordance with embodiments of the present disclosure.

FIG. 7 is a flowchart depicting aspects of the implementation and operation of a sensor system 104 in accordance with embodiments of the present disclosure. Initially, a determination is made as to whether the target area 114 is within the field of view of the sensor 104 (step 704). If not, the sensor system 104 can be moved by moving an associated platform 108, or the sensor system 104 enclosure 204 and/or the steering mirror 220 can be adjusted, to place the target area 114 within the field of view of the sensor system 104 (step 708).

Once the target area 114 is within the field of view of the sensor 104, the light source assemblies 208 are operated to generate light at the desired wavelengths and polarizations (step 712). In particular, the first light source assembly 208a is operated to generate light 406a having a first wavelength and a first polarization, where the first wavelength is significantly absorbed by a gas of interest. The second light source assembly 208b is operated to generate light 406b having a second wavelength and a second polarization, where the second wavelength is not significantly absorbed by the gas of interest. In accordance with embodiments of the present disclosure, a pulse of light 406a of the first wavelength is followed in quick succession by a pulse of light 406b of the second wavelength. For example, a pulse of light 406b of the second wavelength can follow a pulse of light 406a of the first wavelength by about 2 µS or less, where about means within +/−5% of the stated value. As another example, a pulse of light 406b of the second wavelength can be spaced apart from a pulse of light 406a of the first wavelength by about 1 µS or less. This close temporal spacing of the light 406 pulses ensures that essentially the same target area 114 is illuminated, even when the sensor system 104 is mounted to a moving platform 108, such as an airplane.

A pulse of light 406 generated by a light source assembly 208 is placed along a common path 408 (step 716). In accordance with embodiments of the present disclosure, a polarizing beam splitter 412 receives light from the light source assemblies 208, and directs that light along the common path 408. By placing light from the different light source assemblies 208 onto a common path 408, elements within the optical train downstream of the polarizing beam splitter 412 can be shared and used to direct light of either wavelength to the same target area 114. At step 720, the light placed on the common path 408 is circularly polarized. In accordance with at least some embodiments of the present disclosure, light 410 from any of the light source assemblies 208 is circularly polarized in the same direction. As can be appreciated by one of skill in the art after consideration of the present disclosure, by circularly polarizing the different wavelengths of light, the interaction the light with the target area 114 will be substantially the same. At step 722, a portion of the light is picked-off and used to characterize the outgoing pulses. The remaining circularly polarized light 410 is then directed to the target area 114 as transmitted light 116 by the transmit optics 216 (step 724).

The transmitted light 116 passes through the atmosphere within the target volume 106 between the sensor system 104 and the target area 114, including any gas of interest 122 along that path. At least some of the transmitted light 116 is then reflected from a surface or surfaces within the target area 114, and is returned to the sensor system 104 as reflected light 120 (step 728). The reflected light 120 is directed by the steering mirror 220 through the receive telescope 228, which places the light 120 on the detector 224 (step 732).

The detector 224 obtains amplitude information and time of arrival information regarding the reflected light 120 (step 736). Accordingly, the detector 224 operates as a range and amplitude sensor. Where the reflected light 120 is of the first wavelength, the amplitude of that light will be diminished or attenuated by the presence of the gas of interest 122 within the target volume 106. The amount of attenuation due to the presence of the gas of interest 122 rather than to other atmospheric constituents or effects can be determined by comparing the amplitude of the received light of the first wavelength to the amplitude of the light of the second wavelength. In particular, reflected light 120 of the second wavelength is relatively unaffected by the gas of interest 122, and therefore provides the reference amplitude. At step 740, the amplitude of received light of the first wavelength is compared to received light of the second wavelength, and the transmitted light characteristics fed from step 722 via path 723, to obtain information regarding the concentration path length of the gas of interest 122. In either case, the time of arrival of the reflected light 120 at the detector 224 provides information regarding the range of the sensor system 104 from the target area 114. At step 744, information regarding the range for the sensor system 104 to the target area 114 is determined. In particular, by monitoring the time elapsed between the transmission of a pulse of light from the sensor system 104, to the receipt of the reflection of that pulse at the detector 224, the laser and processing section 240 can determine a range of the target area 114 from the sensor system 104. At step 746, the concentration and range information are combined to determine the path-averaged concentration of the gas. In accordance with embodiments of the present disclosure, comparing an amplitude of light of the first wavelength received at the detector 224 to light of the second wavelength received at the detector 224 can be performed by the processor or single board computer 352. Similarly, monitoring the time of flight of a light pulse and calculation of a range between the sensor system 104 and the target area 114 can be performed by the processor or single board computer 352. Alternatively or in addition, some or all of these calculations can be performed by the FPGA 356.

A determination can then be made as to whether operation of the sensor system 104 is to be continued (step 748). If operation is to be continued, the process can return to step 704. Otherwise, the process can end.

Operation of a sensor system 104 in accordance with embodiments of the present disclosure can also include generating and providing output, for example in the form of concentration data regarding a gas of interest 122, information regarding the location at which the gas of interest 122 is detected, and generating and displaying an image depicting the detected emission of a gas of interest to 122 overlaid on or with respect to an image or depiction of the scene 112. Moreover, embodiments of the present disclosure implementing a flash DIAL sensor system 104 can simultaneously combine topography (3D imaging) and gas detection in an integrated single sensor to provide improved spatial resolution and chemical sensitivity at reduced size, weight, and power (SWaP). The adaptation of flash LIDAR technology to add DIAL capability to provide 3D imaging and gas detection simultaneously, in real time, is unique to embodiments of the present disclosure.

The flash LiDAR topographic LiDAR modality uses a single pulse to illuminate a whole scene imaged onto a focal plane array. The flash LiDAR focal plane array observes a pulse waveform from each pixel, giving the capability to calculate pulse time of flight and therefore distance at each pixel. Embodiments of the present disclosure use the same waveform capture at each pixel to capture DIAL by using pulses that are separated in time and that are both on-line and off-line of a targeted spectroscopic absorption feature.

Accordingly, various embodiments of a sensor system 104 in accordance with embodiments of the present disclosure have been described. As can be appreciated by one of skill in the art after consideration of the present disclosure, further embodiments or modifications of embodiments are possible and within the scope of the disclosure. For example, and without limitation, the polarization characteristics and transmission paths of light of different wavelengths can be exchanged. As a further example, at least some aspects of the optical trains with respect to transmitted light and received light can be exchanged, for instance such that transmitted light is reflected from a mirror 236 before being directed to a steering mirror 220, while received light is directed by the steering mirror 220 to receive optics 228 without being reflected by an intervening mirror. Other variations and modifications are also possible.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. A sensor system, comprising:
   a first light source assembly, wherein the first light source assembly is operable to output light at a first wavelength;
   a second light source assembly, wherein the second light source assembly is operable to output light at a second wavelength, wherein the first wavelength is different than the second wavelength;
   a combiner, wherein the light output from the first light source assembly and the light output from the second light source assembly are directed along a common path;
   and
   transmit optics, wherein the first light source assembly includes a first laser, wherein the first light source assembly further includes a first volume Bragg grating (VBG), wherein the first VBG receives light from the first laser and outputs light at the first wavelength, wherein the second light source assembly includes a second laser, wherein the second light source assembly further includes a second VBG, and wherein the second VBG receives light from the second laser and outputs light at the second wavelength.

2. The sensor system of claim 1, wherein the common path includes an optical fiber.

3. The sensor system of claim 1, further comprising:
   a quarter waveplate, wherein the quarter waveplate receives the light directed along the common path, wherein the light output by the first light source assembly has a first polarization, wherein the light output by the second light source assembly has a second polarization that is orthogonal to the first polarization, wherein the combiner is a polarization combiner, and wherein the transmit optics receive light circularly polarized by the quarter waveplate.

4. The sensor system of claim 3, wherein the light output by the first VBG has a first linear polarization, and wherein the light output by the second VBG has a second linear polarization.

5. The sensor system of claim 4, wherein the light output by the first VBG has a first line width, and wherein the light output by the second VBG has a second line width.

6. The sensor system of claim 4, further comprising:
a pick off mirror; and
a laser monitor, wherein the pick off mirror is between the quarter waveplate and the transmit optics, wherein the pick off mirror directs a portion of the light circularly polarized by the quarter waveplate to the laser monitor, and wherein the laser monitor detects a wavelength and energy content of the circularly polarized light.

7. The sensor system of claim 6, wherein the laser monitor includes:
a beam splitter, wherein the beam splitter receives light from the pick off mirror and divides the received light into first and second beams;
a gas cell, wherein the gas cell receives light included in the first beam;
a first integrating sphere, wherein the first integrating sphere receives the light included in the first beam that has passed through the gas cell;
a first detector, wherein the first detector receives light from the first integrating sphere;
a second integrating sphere, wherein the second integrating sphere receives the light included in the second beam; and
a second detector, wherein the second detector receives light from the second integrating sphere.

8. A sensor system, comprising:
a first light source assembly including a first laser, wherein the first light source assembly is operable to output light at a first wavelength;
a second light source assembly including a second laser, wherein the second light source assembly is operable to output light at a second wavelength, and wherein the first wavelength is different than the second wavelength;
a combiner, wherein the light output from the first light source assembly and the light output from the second light source assembly are directed along a common path; and
transmit optics, wherein the transmit optics include a steering mirror.

9. The sensor system of claim 8, further comprising:
a quarter waveplate, wherein the quarter waveplate receives the light directed along the common path, wherein the light output by the first light source assembly has a first polarization, wherein the light output by the second light source assembly has a second polarization that is orthogonal to the first polarization, wherein the combiner is a polarization combiner, wherein the transmit optics receives light circularly polarized by the quarter waveplate, and wherein the steering mirror directs the light circularly polarized by the quarter waveplate towards a target area.

10. The sensor system of claim 9, further comprising:
a receive telescope; and
a detector, wherein light reflected from the target area is received at the receive telescope and passed to the detector.

11. The sensor system of claim 10, wherein the detector is a single pixel detector.

12. The sensor system of claim 10, wherein the detector includes an array of pixels.

13. The sensor system of claim 10, further comprising a processor, wherein the processor determines a time of flight of light output from at least one of the lasers and received at the detector, and wherein the processor receives a signal from the detector regarding an amplitude of the light received at the detector.

14. The sensor system of claim 7, wherein the transmit optics further include:
a multiple mode fiber;
a collimator; and
a diffuser, wherein the fiber receives the light circularly polarized by the quarter waveplate, wherein the collimator receives light from the fiber, wherein the diffuser receives light from the collimator, and wherein a steering mirror receives light from the diffuser.

15. A method for remotely measuring a gas concentration, comprising:
producing light having a first wavelength;
producing light having a second wavelength;
directing the light having a first wavelength and the light having a second wavelength along a common path;
directing the light having the first wavelength to a target area, wherein the light having the first wavelength is produced at a first point in time;
directing the light having the second wavelength to the target area, wherein the light having the second wavelength is produced at a second point in time;
receiving first reflected light at a detector, wherein the first reflected light includes light having the first wavelength;
determining a time of arrival and an amplitude of the light having the first wavelength;
receiving second reflected light at the detector, wherein the second reflected light includes light having the second wavelength;
determining a time of arrival and an amplitude of the light having the second wavelength;
determining a range to the target area from at least one of:
a difference between a time of transmission and the time of arrival of the light having the first wavelength; and
a difference between a time of transmission and the time of arrival of the light having the second wavelength; and
determining a concentration of a gas of interest from a difference between the amplitude of the light having a first wavelength and the amplitude of the light having a second wavelength.

16. The sensor system of claim 8, wherein the common path includes an optical fiber.

17. The method of claim 15, wherein the first point in time is within about 2 microsecond or less of the second point in time.

18. The method of claim 15, wherein the detector is an imaging detector, and wherein the method further includes:
combining three-dimensional image data from the detector with two-dimensional image data from a context camera; and
displaying the combined image data.

19. The method of claim 15, wherein the light of a first wavelength has a first polarization, wherein the light of a second wavelength has a second polarization that is orthogonal to the first polarization, wherein the light of the first polarization and the light of the second polarization is converted to circularly polarized light, and wherein the circularly polarized light is directed to the target area.

20. A remote gas detection system, comprising:
- a first light source assembly, wherein the first light source assembly is operable to output light at a first wavelength;
- a second light source assembly, wherein the second light source assembly is operable to output light at a second wavelength, and wherein the first wavelength is different than the second wavelength;
- a combiner, wherein the light output from the first light source assembly and the light output from the second light source assembly are directed along a common path;
- transmit optics, wherein the transmit optics direct the light output from the first and second tight source assemblies towards a target area;
- a range and amplitude sensor, wherein the range and amplitude sensor receives light reflected from the target area, and wherein the sensor provides a signal indicating a time at which the light reflected from the target area is received and an amplitude of that light;
- an image sensor; and
- a processor, wherein the processor determines a range and concentration of a target gas using the range and amplitude sensor, wherein the processor combines information regarding the range and concentration of the target gas with image information from the image sensor, and wherein the combined information is at least one of stored and displayed.

21. The remote gas detection system of claim 20, further comprising:
- a quarter waveplate, wherein the light output by the first light source assembly has a first polarization, wherein the light output by the second light source assembly has a second polarization that is orthogonal to the first polarization, wherein the combiner is a polarization combiner, wherein the light directed along the common path is circularly polarized by the quarter waveplate, and wherein the light directed towards the target area by the transmit optics is circularly polarized light.

* * * * *